United States Patent
Häni et al.

(10) Patent No.: US 9,555,153 B2
(45) Date of Patent: Jan. 31, 2017

(54) COTTON BUD

(75) Inventors: Beat Häni, Zuzwil (CH); Christian Rytka, Wehr (DE); Guy Petignat, Erlenbach (CH)

(73) Assignee: ROWEG HOLDING AG, Erlenbach ZH (CH)

( * ) Notice: Subject to any disclaimer, the term of this patent is extended or adjusted under 35 U.S.C. 154(b) by 389 days.

(21) Appl. No.: 14/127,303

(22) PCT Filed: Jun. 20, 2012

(86) PCT No.: PCT/CH2012/000135
§ 371 (c)(1),
(2), (4) Date: Feb. 26, 2014

(87) PCT Pub. No.: WO2012/174673
PCT Pub. Date: Dec. 27, 2012

(65) Prior Publication Data
US 2014/0289986 A1     Oct. 2, 2014

(30) Foreign Application Priority Data
Jun. 24, 2011   (CH) ..................... 1077/11

(51) Int. Cl.
| A61F 13/38 | (2006.01) |
| A61L 15/62 | (2006.01) |
| A61L 15/22 | (2006.01) |
| A61L 15/28 | (2006.01) |
| A61L 15/32 | (2006.01) |
| A61L 15/34 | (2006.01) |
| B29C 47/00 | (2006.01) |

(52) U.S. Cl.
CPC ............. *A61L 15/62* (2013.01); *A61F 13/38* (2013.01); *A61F 13/385* (2013.01); *A61L 15/225* (2013.01); *A61L 15/28* (2013.01); *A61L 15/32* (2013.01); *A61L 15/34* (2013.01); *B29C 47/0066* (2013.01)

(58) Field of Classification Search
CPC ............................... A61F 13/385; A61F 13/38
See application file for complete search history.

(56) References Cited

U.S. PATENT DOCUMENTS

| 5,044,383 | A | * | 9/1991 | Alessio | ............... | A45D 29/16 |
| | | | | | | 132/320 |
| 5,902,262 | A | * | 5/1999 | Bastioli | ............... | A61F 13/38 |
| | | | | | | 604/1 |
| 6,254,814 | B1 | * | 7/2001 | Ueda | ............... | C08L 1/02 |
| | | | | | | 264/109 |
| 2003/0040695 | A1 | * | 2/2003 | Zhao | ............... | A61F 13/26 |
| | | | | | | 604/15 |
| 2005/0163944 | A1 | * | 7/2005 | Isshiki | ............... | B32B 7/02 |
| | | | | | | 428/32.39 |
| 2007/0088301 | A1 | * | 4/2007 | Ikeda | ............... | A61F 13/534 |
| | | | | | | 604/368 |

(Continued)

FOREIGN PATENT DOCUMENTS

| DE | 29716819 | 11/1997 |
| EP | 0722705 | 7/1996 |
| WO | 2008012798 | 1/2008 |

*Primary Examiner* — Susan Su
(74) *Attorney, Agent, or Firm* — Rankin, Hill & Clark LLP

(57) ABSTRACT

A cotton bud with a rod-like grip body and with a bud body that is arranged at least at one free end of the grip body. The rod-like grip body is a biologically degradable extrusion body, and includes natural fibers embedded into a material matrix.

13 Claims, 1 Drawing Sheet

(56) References Cited

U.S. PATENT DOCUMENTS

2008/0027367 A1* 1/2008 Abarbanel .......... A61M 35/006
 604/1
2011/0097684 A1* 4/2011 Mark ..................... A61C 5/062
 433/80
2013/0263874 A1* 10/2013 Moody .................. A45D 44/00
 132/200

* cited by examiner

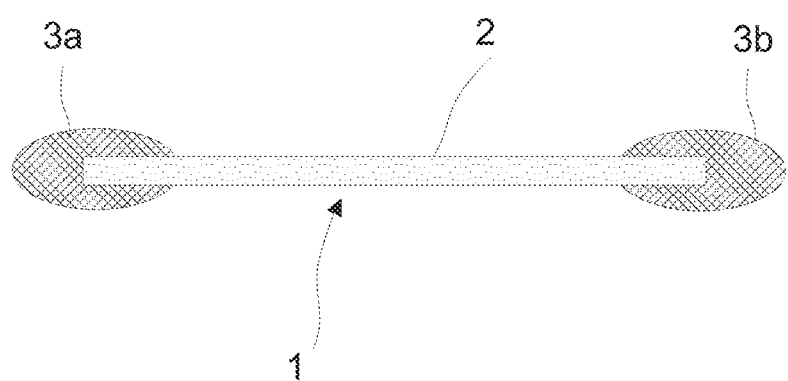

COTTON BUD

BACKGROUND OF THE INVENTION

Field of the Invention

The invention generally lies in the field of hygiene products and care products and more particularly relates to a cotton bud (cotton swab, wadding bud, Q-tip), with a rod-like grip body and with a bud body arranged at least at one free end of the grip body.

Description of Related Art

Cotton buds of the aforementioned type and with bud bodies fastened at both ends are used in a multitude of manners for daily beauty care. Such cotton buds are, in particular, used for cleaning the ears, but are also used with eye cosmetics, manicure, lipstick correction, etc.

With regard to the cotton buds, it is the case of so-called disposable articles, which are led to waste treatment after having been used once. It is therefore desirable for the cotton bud as a whole or at least in part, to be biologically degradable and moreover as a whole or at least in part, to be manufactured of renewable raw materials. Whereas the bud body as a rule consists of natural fibres, such as cotton, the grip body is open manufactured of a plastic which is not biologically degradable, such as polypropylene.

A further demand on such a cotton bud is its inexpensive manufacture. Since with regard to the cotton bud, it is the case of a disposable article, this should be as inexpensive as possible. The price of the cotton bud is composed of the raw material costs as well as manufacturing expense. It is notable that the manufacture of the grip body is a large part of the overall manufacturing costs of the cotton bud.

It is therefore not too surprising that grips bodies of plastic, which are biologically non-degradable and thus less environmentally friendly, but inexpensive to produce, are widespread. Even the manufacture of the grip bodies from plastic requires comparatively little effort and is therefore inexpensive. Thus, for example, DE-A-2 013 886 describes a cotton bud with a grip body of a plastic tube piece which is manufactured with an extrusion method.

Earlier variants of cotton buds of wood are no longer obtainable today. This is due to the fact that the grip body, on account of the application of such care products in eye cosmetics, should not be too rigid or stiff. The grip bodies used nowadays, although still being comparatively stiff, however have a certain pliability or flexibility, so they buckle when a certain bending force is exceeded, but without splintering. The risk of injury with an undesired incorrect manipulation during the application of make-up or during the cleaning of the ears, for example, is reduced on account of this.

DE-U-297 16 819 describes a compostable cotton bud which is manufactured of cardboard or paper. The grip body of cardboard is manufactured by way of this being cut out or punched from a two dimensional cardboard body, or is obtained by way of a cellulose pulp being filled into suitable casting moulds and being pressed. The grip body of paper is manufactured as a wound body, with which paper strips are wound into a rod-like body with suitable winding techniques or technology.

The grip bodies described above either have the disadvantage that they are not environmentally friendly or that their manufacture requires some effort and is accordingly expensive.

SUMMARY OF THE INVENTION

It is therefore the object of the invention, to suggest a cotton bud of the previously mentioned type, which on the one hand is inexpensive to manufacture, but on the other hand comprises a biologically degradable (biodegradable) grip body.

The cotton buds according to the present invention have a rod-like grip body that is a biologically degradable extrusion body and that comprises a material matrix as well as natural fibres that are embedded therein, such as, for example, cellulose fibres, as are obtained, for example, from waste paper, directly from wood and/or rice husks, straw and/or cereal husks.

BRIEF DESCRIPTION OF THE DRAWING

The subject-matter of the invention is represented by way of an embodiment example according to FIG. 1 of the accompanying drawing.

DETAILED DESCRIPTION OF THE PREFERRED EMBODIMENT

The shown cotton bud 1 consists of a rod-like grip body 2 in the form of a biologically degradable extrusion body, as well as of bud bodies 3a, 3b of cotton which are in each case wound around the grip body 2 at both ends.

The material matrix in particular serves as a binding agent that holds together the natural fibres and forms a fibre-reinforced structure with these fibres. The material matrix comprises or consists preferably of one of the subsequently specified, biologically degradable materials. Moreover, the material matrix can also consist of a mixture of these materials or comprise this mixture:

starch, gluten, hemicellulose, sugar, lignin, chitin, gelatine, proteins, wax, glycerine, fructose, methylcellulose, agar-agar, pectin and/or biologically degradable polymers.

Biologically degradable polymers can, for example, be:

biologically degradable copolyesters, such as BTA, in particular blends with further biologically degradable polymers, thermoplastic starch (TPS), starch blends, polyactide or polylactic acid (PLA), and PLA blends, cellulose products such as cellulose acetate (CA), polyhydroxyalkanoates (PHA), polyhydroxybutyric acid (PHB).

biologically degradable polymers based on mineral oil such as polycaprolactone (PCL), biologically degradable polymers which are derived chemically from lignin, chitin, casein, gelatine, proteins generally or vegetable oils, biologically degradable polymers based on modified cellulose derivatives.

The material matrix can moreover be formed by way of dissolving the natural fibres with the help of solvents, so that self-reinforcing cellulose composites arise.

The material matrix in particular serves for the positive-fit, chemical and/or physical cross-linking of the fibres, or for the formation of hydrogen bonds. The share of the material matrix with regard to the volume can be greater, equal or smaller that the share of natural fibres. If the share of natural fibres is significantly predominant, then the natural fibres can even form a fibre mass, whose individual fibres are bonded to one another via the material matrix acting as a binding agent. The material matrix as a result forms a fibre-reinforced structure together with the natural fibres.

The material matrix can be added separately or be already contained in the starting material, so that its function as a binding agent merely has to be activated during the manufacturing process. This is particularly the case if the material matrix, for example, comprises starch, sugar or lignin.

The grip body preferably comprises 10% by volume or more, in particular 30% by volume or more and advantageously 40% by volume or more, of natural fibres. Moreover, the grip body preferably comprises 90% by volume, or less, in particular 80% by volume or less and advantageously 70% by volume or less, of natural fibres. The natural fibres are preferably secondary fibres of recycled fibre material. The natural fibres can, for example, be cellulose fibres as has already been mentioned. The recycled starting material is preferably a biological fibre material which can be obtained very economically and which is obtained, for example, from waste paper or from waste from rice production. Cellulose fibres can, for example, be obtained from ground or frayed waste-paper, i.e. waste-paper is opened up and broken down into cellulose fibres. Moreover, hemicellulose can be also obtained from the waste-paper or from the waste from the production of rice. This ensures, for example, a high tear resistance and tensile strength of the grip body. The natural fibres can also be primary fibres, for example, from wood. A mixture of primary fibres and secondary fibres is also conceivable.

The majority or all of the natural fibres in the grip body are preferably aligned in its longitudinal direction. The alignment of the natural fibres in the longitudinal direction is preferably effected during the extrusion process.

The grip body, apart from the mentioned primarily applied natural fibres, can yet comprise further fibres, in particular long fibres, which have a greater average fibre length than the mentioned natural fibres, for the additional reinforcement of the grip body. The further fibres are preferably vegetable fibres, in particular cotton fibres, hemp fibres or mixtures thereof. Cotton fibres are preferably likewise secondary fibres which, for example, can be recycled fibres from the spinning industry or from waste-textile recycling. The primarily applied natural fibres can, for example, have lengths of greater or equal to 0.1 mm, in particular of greater or equal to 0.5 mm and of smaller or equal to 8 mm, in particular smaller or equal to 5 mm. The further fibres (long fibres) can, for example, have lengths of greater or equal to 5 mm, and smaller or equal to 30 mm, in particular smaller or equal to 20 mm The grip body of the cotton bud preferably has a typical length of 5 to 10 cm. The diameter of the grip body is, for example, 0.5 to 3 mm, in particular 1 to 2 mm. Both ends of the grip body designed as a small rod are wrapped around by cotton fluff. The bud can be of plastic fibres or preferably also of biologically degradable natural fibres such as cotton.

The cross section of the rod-like body can be round (circular, oval) or polygonal. Other cross-sectional shapes are also conceivable. The grip body can moreover be designed as a solid body or hollow body. A comparatively large scope for fashioning exists with regard to the cross-sectional shape of the grip body thanks to the application of an extrusion method.

Moreover, what is defined in the appended claims is also a rod-like grip body that is manufactured from a biologically degradable extrusion body, and comprises natural fibres embedded into a material matrix. All features of the grip body that are disclosed in this description, in the context of its use in cotton buds, also apply to the very generally claimed rod-like grip body. This rod-like grip body, as has already been explained in detail, is preferably applied in cotton buds. The subsequently described manufacturing method should generally also apply to rod-like grip bodies and not only to grip bodies that are applied with cotton buds.

The grip bodies according to the invention moreover can also be applied in the field of foodstuffs, for example, in lolly sticks (lollypops, suckers) for the manufacture of ice cream on a stick. The grip bodies can also be applied in further fields of body hygiene. Thus, the grip body can also be applied in dental care, for example, as a floss holder. A brush head or dental floss, for example, can also be applied at one end of the grip body instead of a bud.

The grip bodies are preferably manufactured in an extrusion device. The extrusion device comprises a mixing device and an extrusion tool, via which the extrusion mass is extruded in a shaping manner. The method for manufacturing the grip body of a cotton bud includes the following steps:

mixing natural fibres with a biologically degradable matrix material into an extrudable extrusion amass in a mixing device;

extruding the extrusion mass through an extrusion nozzle amid the formation of an elongate extrusion body; and, curing of the extrusion body.

The extrusion mass can be highly viscous depending on the matrix. The extrusion mass can also be a dry blend.

The mixing device can be integrated in the extruder. The fibres and matrix for this can be introduced into the extruder, for example, separately via two metering devices.

The components of the material matrix for example are fed in granulate form or in a fluid or flowable form to the extrusion device. The components must be melted as the case may be. Water can be added during the mixing procedure, depending on which substances are applied and in what quantities. The addition of water can, for example, serve for the activation of the already present material matrix or of the binding agent such as lignin, gluten or starch. Moreover, the water addition can serve for the positive-fit cross-linking of fibres. The water addition can moreover serve for forming hydrogen bonds with a subsequent curing (hardening).

The extrusion mass is preferably mixed by way of an extruder screw. The extrusion mass can be premixed in a separate mixing device, the so-called compounder or mixer, even before the extrusion process. The grip body can accordingly be manufactured or extruded by way of a single-screw or double-screw extruder.

The extrusion body can be extruded horizontally or vertically, i.e. in the direction of gravity. The extrusion body exiting from the extrusion nozzle is cut to length into individual grip bodies, before, during or after the curing.

Curing in the broadest sense means the solidification of the extrusion body. The feature curing thus also includes the mere solidification of the extrusion body, i.e., the curing can include a mere drying, cooling and/or a polymerisation.

The cotton pads according to the invention are applied in beauty care or cosmetics, for example, for make-up, in baby care, when cleaning the ears. Moreover, cotton buds according to the invention are also applied as a so-called smear tool, i.e. for smearing saliva samples, such as for determining the genetic fingerprint with DNA mass screening The grip body of the cotton bud according to the invention has the advantage that this has a comparatively high bending stiffness and simultaneously does not break in a splintering manner when the bending forces are too high, but rather deforms plastically. Accordingly, the grip body according to the invention has plastic characteristics. Moreover, the grip body, as already mentioned, is inexpensive in its manufacture, in particular if recycled natural fibres are applied, as well as biologically degradable.

The invention claimed is:

1. A cotton bud with a rod-like grip body and with a bud body that is arranged at least at one free end of the grip body, wherein the rod-like grip body is a biologically degradable extrusion body that comprises cellulose fibres as well as a material matrix, wherein the cellulose fibres are held together via the material matrix acting as a binding agent, wherein apart from the cellulose fibres the grip body comprise long fibres having lengths of greater than or equal to 5 mm for reinforcement of the grip body.

2. The cotton bud according to claim 1, wherein the material matrix acts as a binding agent and comprises a material selected from the group consisting of: starch, sugar, lignin, chitin, gelatine, proteins, glycerine, fructose, methyl cellulose, agar-agar, wax, pectin and/or biologically degradable polymers.

3. The cotton bud according to claim 1, wherein the grip body comprises 10 to 90% by volume of cellulose fibres.

4. The cotton bud according to claim 1, wherein the cellulose fibres are aligned in the longitudinal direction of the rod-like grip body.

5. The cotton bud according to claim 1, wherein the long fibres are cotton fibres.

6. The cotton bud according to claim 1, wherein the cellulose fibres are secondary fibres of a recycled material or comprise secondary fibres of a recycled material.

7. The cotton bud according to claim 1, wherein the cellulose fibres are primary fibres or comprise primary fibres which are obtained directly from wood or wood waste.

8. A rod-like grip body for a cotton bud, wherein the grip body is manufactured from a biologically degradable extrusion body, and comprises cellulose fibres embedded into a material matrix, and wherein, apart from the cellulose fibres, the grip body comprises long fibres having lengths of greater than or equal to 5 mm.

9. A method for manufacturing a rod-like grip body for a cotton bud, said rod-like grip body being manufactured from a biologically degradable extrusion body and comprising cellulose fibres embedded into a material matrix, and wherein, apart from the cellulose fibres, the grip body comprises long fibres having lengths of greater than or equal to 5 mm, the method comprising the steps of:
  mixing cellulose fibres with a biologically degradable matrix material into an extrudable extrusion mass in a mixing device;
  extruding the extrusion mass through an extrusion nozzle amid the formation of an elongate extrusion body;
  curing the extrusion body.

10. The method according to claim 9, wherein water is added during the mixing of the extrusion mass.

11. The method according to claim 9, wherein the extrusion mass is mixed in an extruder screw.

12. The method according to claim 9, wherein the extrusion body is cut to length into individual grip bodies before, during or after the curing.

13. The method according to claim 9, wherein the curing is a solidifying or drying of the extrusion body.

* * * * *